US00PP15575P2

(12) United States Plant Patent
Tobutt

(10) Patent No.: US PP15,575 P2
(45) Date of Patent: Feb. 22, 2005

(54) ***SAMBUCUS* PLANT NAMED 'EVA'**

(50) Latin Name: *Sambucus nigra*
Varietal Denomination: Eva

(75) Inventor: Kenneth Richard Tobutt, Meopham (GB)

(73) Assignee: Horticulture Research International, East Malling (GB)

( * ) Notice: Subject to any disclaimer, the term of this patent is extended or adjusted under 35 U.S.C. 154(b) by 31 days.

(21) Appl. No.: 10/453,412

(22) Filed: Jun. 3, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—Mark P. Bourgeois

(57) ABSTRACT

A new cultivar of *Sambucus nigra* plant named 'Eva' that is particulary distinguished in having foliage that combines very dark purple color with a laciniate shape.

2 Drawing Sheets

Botanical classification: *Sambucus nigra*.
Variety denomination: 'Eva'.

BACKGROUND OF THE INVENTION

This new invention presents a new cultivar of Elderberry, *Sambucus nigra*, herein referred to as 'Eva'. 'Eva' is unique in that its leaves combine very dark purple almost black, colour with laciniate shape. 'Eva' resulted from a breeding programme conducted at Horticulture Research International, East Malling, West Malling, Kent in England. The two first generation crosses (148 and 149) were made in 1988 between 'Laciniata' (unpatented) and 'Guincho Purple' (unpatented), and between 'Laciniata' and 'Aurea', (unpatented). 'Laciniata' has green laciniate leaves; 'Guincho Purple' and 'Aurea' have purple and yellow pinnate leaves respectively. The next cross (391) was made in 1991 between a purple leafed seedling of the former progeny (148) and a yellow leafed seedling of the latter (149). The third cross (595) was made in June 1995 between two seedlings of progeny 391 with laciniate leaves, one with tawny leaves identified as 391A and one with purple leaves identified as 391B. Approximately 200 flowers were hand-pollinated and then bagged for protection until seed could be harvested. The collected seed was germinated and resulted in 39 seedlings being planted out in 1997 for evaluation. Out of this progeny, selection 595-35 was selected as a single plant in 1998 for further trialing on the basis of its dark purple, almost black, laciniate foliage. Selection 595-35 was first propagated by softwood cuttings from the originally discovered plant by the inventor in East Malling in 1998 and planted in trial in 1999. In 2001 it was confirmed as worthy of release under the name 'Eva' and in subsequent propagation has been found to remain true to type in successive generations.

SUMMARY OF THE INVENTION

The following characteristics have been repeatedly observed and represent the attributes of the new cultivar. These characteristics in combination distinguish this cultivar from its parents and others cultivars currently available in commerce.

1. The foliage of 'Eva' is a very dark purple with purple veins and purple stems. It is darker than 'Guincho Purple'(unpatented) and similar to 'Gerda' (U.S. plant Pat. No. 12,305).
2. The leaves of 'Eva' are laciniate whereas those of 'Guincho Purple' and 'Gerda' are pinnate.

'Eva' is distinguished from the female parent 391B in that 'Eva' has dark purple leaves.

'Eva' is distinguished from the male parent 391A in that 'Eva' has dark purple leaves.

BRIEF DESCRIPTION OF THE DRAWINGS

The first sheet contains a photo of a two year old example of *Sambucus nigra* 'Eva' as grown in the landscape in East Malling, Kent, England.

The second sheet shows a close-up of the fully open flowers.

The colour is as accurate as possible by conventional photography.

BOTANICAL DESCRIPTION OF THE PLANT

The following is a detailed description of the new cultivar as field grown outdoors in East Malling, Kent, England. The plants were 5 years old. Phenotypic differences may be observed with variations in environmental, climatic, and cultural conditions. The colour determination is in accordance with The Royal Horticultural Society (R.H.S.) Colour Chart of The Royal Horticultural Society, London, England, except where general colour terms of ordinary dictionary significance are used.

Botanical classification: 'Eva' is a cultivar of *Sambucus nigra* belonging to the Caprifoliaceae family.
Commercial classification: Elderberry.
Parentage:
Seed parent: Proprietary selection 391B.
Pollen parent: Proprietary selection 391A.
Plant description:

*Blooming period.*—May to July in the Uk with flowers lasting two to three weeks.

*Crop time.*—Approximately 1 year to produce a flowering plant.

*Plant habit.*—Upright, dense shrub, slightly spreading, vigorous.

*Height and spread.*—3 m in height and spread if left un-pruned.

*Hardiness.*—Has been found to tolerate UK climatic conditions with temperatures typically in the range −5° C. to +30° C. Zone 4–9.

*Type.*—Deciduous shrub.

*Root system.*—Fibrous.

*Propagation.*—Nodal or inter-nodal softwood cuttings inserted into coarse free draining compost with bottom heat (~20° C.) and top heat (~18° C), keeping the leaves wet (95–100% humidity) with fine mist, shaded from direct light, day length set at 16 hours. Roots typically appear after 14 days; plants rooted and ready to wean after 28 days, fully weaned after 40 days.

*Culture.*—Sunny to part-shade location, moist but well-drained, moderately fertile soils. Can be pruned to control vigour and shape.

*Diseases and pests.*—No known unique susceptibility or resistance.

Stems: Young stems are green (144A) becoming purple (187A). Shoots 1 to 2 years old are silver grey (201A to 201C) and are smooth except for large grey lenticels (~2 mm in diameter, ~8 per square inch), 80 cm in length and 8 mm in diameter, solid white pith. Older branches have rough furrowed grey-brown (199B) bark;

*Internode length.*—25 cm.

Leaves:

*Shape and division.*—Primarily pinnate (usually 7 leaflets), each leaflet being laciniate, and having approximately 5 lobes.

*Leaf size.*—25 cm in length and 20 cm in width.

*Leaflet base.*—Acute.

*Leaflet tip.*—Acute.

*Margins.*—Serrulate.

*Surface.*—Glossy, metallic.

*Size.*—Leaflets are 10–12 cm long and 6–8 cm in width.

*Colour.*—Leaf buds are 187A. The young, unexpanded, foliage is green (144A) with a peripheral purpling. The mature foliage is dark purple (200A-202A) on the upper surface and a grey-green (191A) on the lower surface. Veins are 187A on the upper side and 187A-186D on the lower side. Autumn foliage colour is 200A-166B on the upper surface and 192A on the lower surface.

Flowers:

*Inflorescence type.*—Flat polychasium, umbel-like cyme, average 20 cm in diameter and 3 cm in depth, 400 flowers per inflorescence.

*Flower structure.*—Rotate shape with 5 orbicular petals, 2 mm in width, margin entire, petal base rounded, petal apex rounded., petals alternating with the 5 anthers, pistil one in number, style disk like and very short, ~ 1 mm. Stigma: Minimal, < 1 mm diameter. Pollen: Pale yellow colour (~4D), abundant in quantity.

*Flower size.*—~3 mm from ovary base to anther tip, diameter of corolla 6 mm.

*Flower colour.*—Upper surfaces of young petals are white flushed pink (72B-63C), at tips, fading to white 155D with age; underside of petals are 72B to 63C at distal edge, paler at the base fading at centre. Undehisced anthers are 45A.

*Sepals.*—5, triangular shaped, 0.5 mm in length and 0.5 mm in width, 187A in color.

*Bud.*—Globose in shape, 2 mm in diameter, 186A in color.

Fruit:

*Colour.*—Very dark ruby purple surface (59A-187A), flesh light green 145B.

*Shape.*—Globose.

*Presence.*—August–October in the UK.

*Size.*—7 mm in diameter.

*Weight per berry.*—0.25 grams.

*Soluable solids.*—9 percent.

*Fruit produced per plant.*—5 kilograms per year.

*Harvest time.*—August 15 to September 30.

Seeds:

*Number, colour and size.*—Approximately three straw coloured seeds ~2 mm×3 mm per drupe.

It is claimed:

1. A new and distinct cultivar of *Sambucus nigra* plant named 'Eva' as described and illustrated.

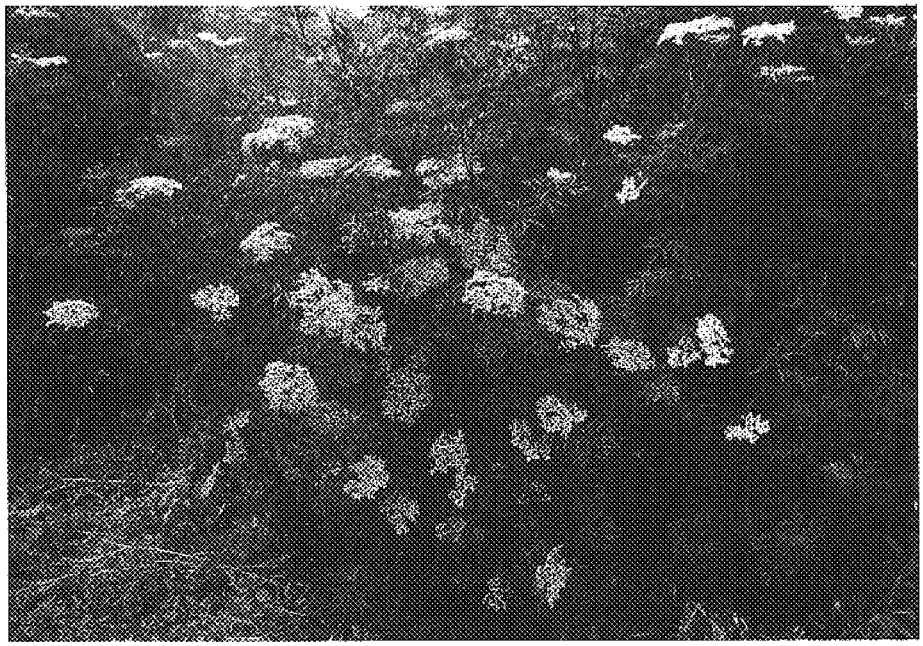

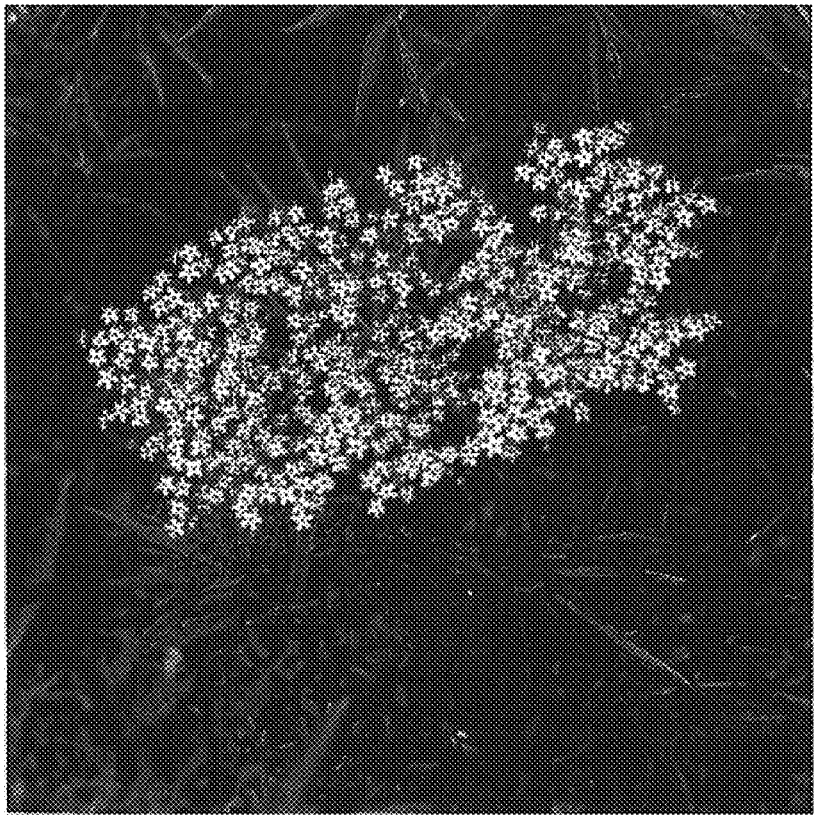

* * * * *